US008324161B2

(12) United States Patent
Godfroid et al.

(10) Patent No.: US 8,324,161 B2
(45) Date of Patent: Dec. 4, 2012

(54) LEUKOTRIENE B4 BINDING SOLUBLE LIPOCALIN RECEPTOR FROM IXODES RICINUS

(75) Inventors: Edmond Godfroid, Brussels (BE); Jérôme Beaufays, Braine-le-comte (BE); Luc Vanhamme, Court-saint-etienne (BE); Benoît Adam, Brussels (BE); Laurence Lins, Vieusart (BE); Sébastien Santini, Ollieres (FR); Robert Brasseur, Meux (BE)

(73) Assignees: Universite Libre de Bruxelles, Brussels (BE); Faculte Universitaire des Sciences Agronomiques de Gembloux, Gembloux (BE)

( * ) Notice: Subject to any disclaimer, the term of this patent is extended or adjusted under 35 U.S.C. 154(b) by 0 days.

(21) Appl. No.: 12/677,420

(22) PCT Filed: Sep. 10, 2008

(86) PCT No.: PCT/EP2008/061988
§ 371 (c)(1),
(2), (4) Date: Oct. 28, 2010

(87) PCT Pub. No.: WO2009/034103
PCT Pub. Date: Mar. 19, 2009

(65) Prior Publication Data
US 2011/0033469 A1    Feb. 10, 2011

(30) Foreign Application Priority Data
Sep. 10, 2007 (EP) .................................. 07116024

(51) Int. Cl.
*A61K 38/00* (2006.01)
*A61K 38/16* (2006.01)
*C07K 1/00* (2006.01)
(52) U.S. Cl. .... 514/12.2; 514/21.2; 530/350; 530/88.91
(58) Field of Classification Search ........................ None
See application file for complete search history.

(56) References Cited

U.S. PATENT DOCUMENTS
6,544,518 B1    4/2003    Friede et al.

FOREIGN PATENT DOCUMENTS

| EP | 1 270 589 A1 | 1/2003 |
|---|---|---|
| WO | WO 01/85166 A1 | 11/2001 |
| WO | WO 02/30458 A1 | 4/2002 |
| WO | WO 2006/123155 A2 | 11/2006 |
| WO | WO 2006/123155 A3 | 11/2006 |
| WO | WO 2007/068907 A2 | 6/2007 |
| WO | WO 2007/068907 A3 | 6/2007 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Frantz. Nature Reviews Drug Discovery 2003, 2: 501.*
Matthys et al. 2000. J. Leukocyte Biol. 68:447-45.*
Pettit et al 1998. Trends in Biotech. 16:343-349.*
Hicks et al. (2007. Expert Opin Invest Drugs 16:1909-1920.*
"Ixodes pacificus clone IP_7_60_92_97 CLU putative secreted histamine binding protein of 22.8 kDa mRNA, complete cds," Aug. 11, 2004: XP-002473386.
"Purative secreted histamine binding protein of 22.8 kDa," Sep. 13, 2004: XP-002473419.
Altschul et al., "Basic local alignment search tool," *J. Mol. Biol.* (1990) 215: 403-410.
Carrillo et al., "The multiple sequence alignment problem in biology," *Siam J. Appl. Math* (1988) 48 (5): 1073-1082.
Franischetti et al., "The transcriptome of the salivary glands of the female western black-legged tick *Ixodes pacificus* (Acari: Ixodidae)," *Insect Biochemistry and Molecular Biology* (2005) 35: 1142-1161.
Gentz et al., "Bioassay for trans-activation using purified human immunodeficiency virus tat-encoded protein: Trans-activation requires mRNA synthesis," *PNAS* (19899) 86 (3): 821-824.
Mans, B.J., "Tick histamine-binding proteins and related lipocalins: Potential as therapeutic agents," *Current Opinion in Investigational Drugs* (2005) 6 (11): 1131-1135. XP009097529.
Nakayama et al., "New serine protease inhibitors with leukotriene $B_4$ ($LTB_4$) receptor binding affinity," *Bioorganic & Medicinal Chemistry* (1997) 5 (5): 971-985. XP001181712.
Nohgawa et al., "Leukotriene $B_4$-activated human endothelial cells promote transendothelial neutorophil migration," *Journal of Leukocyte Biology* (1997) 62: 203-209.
Paesen et al., "Tick Histamine-binding proteins; Isolation, cloning, and three-dimensional structure," *Molecular Cell* (1999) 3: 661-671. XP002473385.
Prevot et al., "Protective immunity against *Ixodes ricinus* induced by a salivary serpin," *Vaccine* (2007) 25: 3284-3292.
Rattan et al., "Protein synthesis, posttranslational modifications, and aging," *Annals of the New York Academy of Sciences* vol. 663, Aging and Cellular Defense Mechanisms pp. 48-62, Nov. 1992.
Seifter et al. "Analysis for protein modifications and nonprotein cofactors," *Methods in Enzymology* (182) 626-646. 1990.
Warlow et al., "Solubilzation and characterization of moderate and high affinity histamine binding sites on human blood mononuclear cells," *Molecular Immunology* (1987) 24 (1): 27-37.
Wolff et al., "Direct gene transfer into mouse muscle in Vivo," *Science* (1990) 247 (4949): 1465-1468.
Yamamoto et al., "Transietn calcium elevation in polymorphonuclear leukocytes triggered by thrombin-activated platelets," *Eur. J. Haematol* (1992) 196-201.
Yokomizo et al., "Hydroxyeicosanoids bind to and activate the low affinity leukotriene $B_4$ receptor, BLT2," *The Journal of Biological Chemistry* (2001) 276 (15): 12454-12459.

* cited by examiner

*Primary Examiner* — Shulamith H Shafer
(74) *Attorney, Agent, or Firm* — Merchant & Gould P.C.

(57) ABSTRACT

Leukotriene B4 binding polypeptide is obtained from Ixodes ricinus. Leukotriene B4 polypeptide, the polynucleotide encoding Leukotriene B4 polypeptide, and Leukotriene B4 polypeptide related polypeptides may be used as research reagents and for treatments and diagnostics specific to animal and human diseases.

8 Claims, 6 Drawing Sheets

LTB4-LIR nucleotide acid sequence.

```
1   ATGCTTAGAA TAGCGGTGGT TGCAGCTTTG TGTTGCTTCG GCACCGGAAC
51  AGTGTCACGT TTTCAGCAAA ACGCGACAGA GCGTCATTAC CAAGAACTGA
101 ATTCTAACCT CTCAAAGTAC CAAGATGCTT GGAAGTCAAA TACTGAAAAT
151 GCAGAGTACG TACTGGCGTA CCGCACTTTT CAAGATATTG AAAGGACACG
201 TATTCGTAGA TGCGTGAGTG CTACATTGCG ATACAAAAAT AAGAAGAACC
251 GAACCACAGT GCACCGGCTG CGATACTATA ACACAAGAGA CCGAAAATGG
301 GAAGGTCATA GTGTACTAAC AAGGTTTAAT GCCACACCAG GCTATACGGT
351 TCCCAACCTA ATGCTAATGT CATCATATCA CAACGAAAGT GATGAAGGAA
401 GGTTATATTG GACCTTGTAC TCTCAATACG GATCTTGCAA CATCGTCAGA
451 GTTGAACGAA ACGGCGGTTG CGAGCTGTGG GTGAGAAAAG GCTTACAAGA
501 CTACATATCA AGCTGCTGTT GGTTCATCTA TAAATCTTAC TGTGGAAATG
551 AGAACTACCA AATATACAAT ACCACGTACT GCAAACGCAA GGGACCCGAG
601 TGA (SEQ ID NO: 1)
```

LTB4-LIR amino acid sequence.

```
1   MLRIAVVAAL CCFGTGTVSR FQQNATERHY QELNSNLSKY QDAWKSNTEN
51  AEYVLAYRTF QDIERTRIRR CVSATLRYKN KKNRTTVHRL RYYNTRDRKW
101 EGHSVLTRFN ATPGYTVPNLM LMSSYHNES DEGRLYWTLY SQYGSCNIVR
151 VERNGGCELW VRKGLQDYISS CCWFIYKSY CGNENYQIYN TTYCKRKGPE
(SEQ ID NO: 2)
```

LIR = LTB4-LIR polypeptide

SEQUENCE LISTING

```
<160> NUMBER OF SEQ ID NOS: 4

<210> SEQ ID NO 1
<211> LENGTH: 603
<212> TYPE: DNA
<213> ORGANISM: Ixodes ricinus
<220> FEATURE:
<221> NAME/KEY: CDS
<222> LOCATION: (1)..(603)

<400> SEQUENCE: 1 atg ctt aga ata gcg gtg gtt gca gct ttg tgt tgc ttc ggc acc gga      48
Met Leu Arg Ile Ala Val Val Ala Ala Leu Cys Cys Phe Gly Thr Gly
1               5                   10                  15 aca gtg tca cgt ttt cag caa aac gcg aca gag cgt cat tac caa gaa      96
Thr Val Ser Arg Phe Gln Gln Asn Ala Thr Glu Arg His Tyr Gln Glu
            20                  25                  30 ctg aat tct aac ctc tca aag tac caa gat gct tgg aag tca aat act     144
Leu Asn Ser Asn Leu Ser Lys Tyr Gln Asp Ala Trp Lys Ser Asn Thr
```

```
                     35                  40                  45
gaa aat gca gag tac gta ctg gcg tac cgc act ttt caa gat att gaa    192
Glu Asn Ala Glu Tyr Val Leu Ala Tyr Arg Thr Phe Gln Asp Ile Glu
 50                  55                  60 agg aca cgt att cgt aga tgc gtg agt gct aca ttg cga tac aaa aat    240
Arg Thr Arg Ile Arg Arg Cys Val Ser Ala Thr Leu Arg Tyr Lys Asn
 65                  70                  75                  80 aag aag aac cga acc aca gtg cac cgg ctg cga tac tat aac aca aga    288
Lys Lys Asn Arg Thr Thr Val His Arg Leu Arg Tyr Tyr Asn Thr Arg
                 85                  90                  95 gac cga aaa tgg gaa ggt cat agt gta cta aca agg ttt aat gcc aca    336
Asp Arg Lys Trp Glu Gly His Ser Val Leu Thr Arg Phe Asn Ala Thr
            100                 105                 110 cca ggc tat acg gtt ccc aac cta atg cta atg tca tca tat cac aac    384
Pro Gly Tyr Thr Val Pro Asn Leu Met Leu Met Ser Ser Tyr His Asn
        115                 120                 125 gaa agt gat gaa gga agg tta tat tgg acc ttg tac tct caa tac gga    432
Glu Ser Asp Glu Gly Arg Leu Tyr Trp Thr Leu Tyr Ser Gln Tyr Gly
130                 135                 140 tct tgc aac atc gtc aga gtt gaa cga aac ggc ggt tgc gag ctg tgg    480
Ser Cys Asn Ile Val Arg Val Glu Arg Asn Gly Gly Cys Glu Leu Trp
145                 150                 155                 160 gtg aga aaa ggc tta caa gac tac ata tca agc tgc tgt tgg ttc atc    528
Val Arg Lys Gly Leu Gln Asp Tyr Ile Ser Ser Cys Cys Trp Phe Ile
            165                 170                 175 tat aaa tct tac tgt gga aat gag aac tac caa ata tac aat acc acg    576
Tyr Lys Ser Tyr Cys Gly Asn Glu Asn Tyr Gln Ile Tyr Asn Thr Thr
        180                 185                 190 tac tgc aaa cgc aag gga ccc gag tga                                603
Tyr Cys Lys Arg Lys Gly Pro Glu
        195                 200

<210> SEQ ID NO 2
<211> LENGTH: 200
<212> TYPE: PRT
<213> ORGANISM: Ixodes ricinus

<400> SEQUENCE: 2

Met Leu Arg Ile Ala Val Val Ala Ala Leu Cys Cys Phe Gly Thr Gly
  1               5                  10                  15

Thr Val Ser Arg Phe Gln Gln Asn Ala Thr Glu Arg His Tyr Gln Glu
                 20                  25                  30

Leu Asn Ser Asn Leu Ser Lys Tyr Gln Asp Ala Trp Lys Ser Asn Thr
             35                  40                  45

Glu Asn Ala Glu Tyr Val Leu Ala Tyr Arg Thr Phe Gln Asp Ile Glu
 50                  55                  60

Arg Thr Arg Ile Arg Arg Cys Val Ser Ala Thr Leu Arg Tyr Lys Asn
 65                  70                  75                  80

Lys Lys Asn Arg Thr Thr Val His Arg Leu Arg Tyr Tyr Asn Thr Arg
                 85                  90                  95

Asp Arg Lys Trp Glu Gly His Ser Val Leu Thr Arg Phe Asn Ala Thr
            100                 105                 110

Pro Gly Tyr Thr Val Pro Asn Leu Met Leu Met Ser Ser Tyr His Asn
        115                 120                 125

Glu Ser Asp Glu Gly Arg Leu Tyr Trp Thr Leu Tyr Ser Gln Tyr Gly
130                 135                 140

Ser Cys Asn Ile Val Arg Val Glu Arg Asn Gly Gly Cys Glu Leu Trp
145                 150                 155                 160
```

```
Val Arg Lys Gly Leu Gln Asp Tyr Ile Ser Ser Cys Cys Trp Phe Ile
            165                 170                 175

Tyr Lys Ser Tyr Cys Gly Asn Glu Asn Tyr Gln Ile Tyr Asn Thr Thr
            180                 185                 190

Tyr Cys Lys Arg Lys Gly Pro Glu
        195                 200

<210> SEQ ID NO 3
<211> LENGTH: 29
<212> TYPE: DNA
<213> ORGANISM: Artificial
<220> FEATURE:
<223> OTHER INFORMATION: Synthetic primer

<400> SEQUENCE: 3
gccaccatgc ttagaatagc ggtggttgc                                      29

<210> SEQ ID NO 4
<211> LENGTH: 21
<212> TYPE: DNA
<213> ORGANISM: Artificial
<220> FEATURE:
<223> OTHER INFORMATION: Synthetic primer

<400> SEQUENCE: 4
ctcgggtccc ttgcgtttgc a                                              21
```

LEUKOTRIENE B4 BINDING SOLUBLE LIPOCALIN RECEPTOR FROM IXODES RICINUS

This application is a National Stage Application of PCT/EP2008/061988, filed Sep. 10, 2008, which claims benefit of Serial No. 07116024.6, filed Sep. 10, 2007 in the EPO and which applications are incorporated herein by reference. To the extent appropriate, a claim of priority is made to each of the above disclosed applications.

FIELD OF THE INVENTION

The present invention is related to a new leukotriene B4 binding polypeptide (LTB4-LIR) as well as to its pharmaceutical use.

BACKGROUND OF THE INVENTION AND STATE OF THE ART

The lipocalin family is a large group of small extracellular proteins, having a great diversity at the sequence level. Despite the sequence dissimilarity, their structures are highly conserved.

Based on the conservation of three structurally conserved regions (SCRs), they are divided into two groups. The core set of lipocalins, called 'kernel', are quite closely related proteins and share the three SCRs. The more divergent lipocalins, called outliers, match no more than two of the SCRs.

The lipocalins exhibit great functional diversity. They are implicated in modulation of the immune response, regulation of cell homoeostasis and in the clearance of endogenous and exogenous compounds. They have roles in retinol and pheromone transport, olfaction, invertebrate coloration and prostaglandin synthesis.

Lipocalins have been shown to bind a number of molecules implicated in homeostasis, as retinoids, arachidonic acid and various steroids, in message transmission between individuals as pheromones, in olfactory and gustatory functions and in pigmentation. A small ligand can be enclosed deep within the cavity, while bigger ones interact with the upper loops and even protrude out of the protein to interact with the solvent. Some lipocalins seem to be adapted to the recognition of an individual ligand, while others can bind a broad diversity of molecules.

In addition, eicosanoids are potent lipid mediators involved in inflammation and derived from phospholipase-released arachidonic acid. These include leukotrienes, prostaglandins, thromboxanes, prostacyclins and lipoxins. Leukotrienes are predominantly synthesised by inflammatory cells like granulocytes, mast cells and macrophages.

Four major leukotrienes are implicated in inflammation, i.e. leukotriene B4, C4 (LTC4) and D4 (LTD4) and E4 (LTE4).

LTB4 is a potent chemotactic factor for neutrophils. It also induces their activation, causing degranulation and superoxide generation. Additionally, it participates to the trafficking of T lymphocytes, it enhances macrophage and neutrophil phagocytosis, and promotes the elaboration of other inflammatory mediators, such as cytokines and chemokines. Furthermore, experimental and genetic studies suggest a major role of leukotrienes in atherosclerosis and in its ischemic complications such as acute coronary syndromes and stroke.

Several lipocalins, implicated in the modulation of the host hemostatic and inflammatory systems, have been identified in blood sucking arthropods. Lipocalins in *Rhodnius prolixus* were shown to bind serotonin, ADP, NO and in *Rhipicephalus appendiculatus*, three were shown to bind histamine; but no one appeared to bind leukotriene B4.

Publication from Francischetti et al (Insect Biochemistry and Molecular Biology, Elsevier Science Ltd, volume 35, nr 10, pages 1142-1161, 2005) describes putative secreted histamine-binding proteins.

It would thus appear that said molecule, which upon successful expression, would constitute appropriate antigens for anti-tick vaccines and/or new therapeutic agents.

AIMS OF THE INVENTION

A first aim of the present invention is to provide new compounds which could be used for improving the treatment and/or the prevention of various diseases, especially for reducing activation of cells involved in inflammatory response in particular in pathologies such as ischemy, atherosclerosis and in its ischemic complications such as acute coronary syndromes and stroke, inflammations such as chronic obstructive pulmonary disease, rheumatoid arthritis and septic shock, allograft rejection, cystic fibrosis, psoriasis, liver diseases, renal diseases and immunological disorders.

The aim of the present invention is also to provide such compounds which may be used as suitable antigenic candidates for vaccination against ticks and for blocking transmission of various micro-organisms, especially pathogenic agents carried by ticks.

SUMMARY OF THE INVENTION

A first aspect of the present invention is related to a (poly) peptide which presents more than 50%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity with the amino-acid sequence SEO ID NO: 2, especially a leukotriene B4 binding (poly) peptide comprising or consisting of the amino-acid sequence SEQ ID NO: 2 or an active leukotriene B4 binding fragment thereof (presenting the same leukotriene B4 properties than the full sequence), (possibly) the (poly) nucleotide encoding this (poly) peptide, a vector comprising this (poly) nucleotide or this (poly) peptide, a cell transfected or comprising these vectors and/or an antibody (including a nanobody, an affibody or an hypervariable portion thereof) directed against this (poly) peptide or (poly) nucleotide for use as a medicament (possibly in a pharmaceutical composition comprising an adequate pharmaceutical carrier (or diluent) and a sufficient amount of this (poly) peptide, (poly) nucleotide vector, cell or antibody according to the invention).

Preferably, this (poly)peptide, (poly)nucleotide vector, cell or antibody, pharmaceutical composition is used for the manufacture of a medicament in the treatment and/or the prevention of an inflammatory response (inflammation) of a mammal (including a human) especially for reducing activation of cells involved in an inflammatory response to a pathology, especially in the treatment and/or the prevention of a pathology selected from the group consisting of ischemy, atherosclerosis (and in its ischemic complications), allograft rejection, cystic fibrosis, psoriasis, inflammatory diseases, especially acute coronary syndromes and stroke, allograft rejection, cystic fibrosis, psoriasis, ischemic diseases and inflammatory diseases, such as chronic obstructive pulmonary diseases, rheumatoid arthritis, septic shock and immunological disorders.

Another aspect of the present invention is related to a specific (poly) peptide which presents more than 95%, 96%, 97%, 98%, 99% or 100% sequence identity with the amino-acid sequence SEQ ID NO: 2, especially a leukotriene B4 binding (poly) peptide comprising or consisting of the amino-acid sequence of SEQ ID NO: 2 or an active leukotriene B4 binding fragment thereof (i.e. a leukotriene B4 binding fragment presenting the same possible application than the full length amino-acid sequence SEQ ID NO: 2).

Another aspect of the present is related to a (poly)nucleotide encoding the (poly)peptide according to the invention, a vector comprising this (poly)nucleotide or this (poly)peptide, a cell transfected or comprising the vector according to the invention, an inhibitor being an antibody, a nanobody, an affibody or an hypervariable portion thereof directed against the (poly)peptide or the (poly)nucleotide according to the invention and an hybridoma cell producing this inhibitor (this antibody, nanobody, affibody or an hypervariable portion thereof).

A last aspect of the present invention is related to a pharmaceutical composition comprising an adequate pharmaceutical carrier and an element selecting from the group consisting of the (poly)peptide according to the invention, the (poly) nucleotide according to the invention, the vector according to the invention, the cell according to the invention or the inhibitor (antibody, nanobody or affibody) according to the invention, as well as the use of this pharmaceutical composition for the manufacture of a medicament in the treatment and/or the prevention of the above-mentioned diseases or in the treatment and/or the prevention of diseases induced by tick or pathogenic agents transmitted by tick, especially but not only, *Ixodes ricinus*.

DETAILED DESCRIPTION OF THE INVENTION

The present invention is related to an isolated and purified (preferably soluble) leukotriene B4 binding receptor obtained from the tick *Ixodes ricinus*.

The present invention is also related to molecules (polypeptides) which present a sequence identity higher than 50%, 60%, 65%, 70%, 75%, 85%, 90%, 95%, 96%, 97% or 98%-99% sequence identity with the amino acid sequence SEQ ID NO: 2.

The present invention is also related to a (poly)nucleotide sequence (nucleic acid sequence) encoding said (poly)peptides and their variants, preferably a (poly)nucleotide sequence which presents more than 50%, 60%, 65%, 70%, 75%, 80%, 85%, 90%, 95%, 96%, 97%, 98%-99% or 100% (sequence identify) with the nucleotide sequence SEQ.ID.NO.1 or its complementary strand.

Preferably, said (poly)peptides and their encoding (poly) nucleotides correspond to the complete sequence SEQ.ID.NO.1 or one or more of their active fragments or variants thereof (molecules which present the same or a similar leukotriene B4 binding activity than the complete sequence).

Fragments or variants of the (poly)peptide(s) according to the invention are also molecules which present the same leukotriene B4 binding activity than the native isolated sequence with one or more genetic modifications (such as deletion or addition of one or more nucleotides or amino-acids) in the complete sequence SEQ.ID.NO.1, such as naturally occurring allelic variants, but also sequences affected by the degeneration of the genetic code. Such modifications do not modify the above mentioned percentage of sequence identity.

Said variants are also molecules which present a similar leukotriene B4 binding to the polypeptides according to the invention through the same biochemical pathway and acting similarly upon the same active site, but possibly presents in other homologous sequences of other species which are also included in the present patent protection.

The polypeptides can be also integrated as "native" protein or are part of a fusion protein or may advantageously include additional amino-acid sequences which contain secretory or leader sequences, prosequences, sequences which elute in purification such as multiple histidinoresidue or an additional sequence for stability during recombinant production (tag His in the C-terminal sequence).

Said polypeptides may comprise also marker sequences which facilitate purification of the fuse polypeptide with a sequence as an hexa-histidine peptide as provided in the PQE vector (Invitrogen Inc.) and described by Gentz et al., Proceeding National Academic of Science of the USA, 1989, Vol. 86, pp. 821-824) or an HA tag or glutathione-S transferase. The corresponding polynucleotide may also contain non-coding 5' and 3' sequences such as transcribed non-translated sequences, splicing and poly-adenylation signal and ribosome binding sites.

Another aspect of the present invention is related to a vector comprising the (poly)nucleotide or (poly)peptide according to the invention, said vector being preferably a plasmid, a virus, a liposome or a cationic vesicle able to transfect a cell and to obtain the expression of said (poly) nucleotide by said cell.

A further aspect of the present invention concerns the cell (prokaryotic or eukaryotic cell) transfected by or comprising said vector.

A further aspect of the present invention is related to an inhibitor or ligand (different from the natural ligand (leukotriene B4)) directed against the (poly)peptide according to the invention, a fragment (epitope) thereof or a (poly)nucleotide encoding said (poly)peptide.

Preferably, said inhibitor is an antibody (monoclonal or polyclonal antibody), a nanobody or an active hypervariable portion (Fab', Fab.sub.2, etc.) thereof. The inhibitor could be also a specific receptor of a blood cell able to interact specifically with said polypeptide or its epitopes. The inhibitor could be also an antisense RNA, mIRNA or a ribozyme directed against the polynucleotide encoding said polypeptide.

The present invention is also related to the cells (hybridomas) expressing and producing said antibody, nanobody, or a specific hypervariable portion (Fab', $Fab_2$, etc.) thereof.

A further aspect of the present invention is related to a pharmaceutical composition (including a vaccine) comprising an adequate pharmaceutical carrier (or diluent) and at least one of the various elements according to the invention, especially the polypeptide(s), the variant(s), the encoding polynucleotide(s), their active portions, the vector, the cell transformed by said vector or the inhibitor (or ligand) according to the invention.

Said pharmaceutical composition may comprise also a suitable adjuvant, antioxidant buffer, bacteriostatics and solutions which become biotonic with the blood of the recipient and aqueous and non-aqueous sterile suspensions (which may include suspension agents). The adjuvant used in the pharmaceutical composition is advantageously used for modulating the immune response of a mammal (including a human) in order to improve the characteristic of the pharmaceutical composition according to the invention or to reduce its possible side effects. The suitable pharmaceutical carrier or diluent is selected by the person skilled in the art according to the type of administration to the mammal (oral administration, intravenous administration, intradermal administration, intramuscular administration, peritoneal administration, etc.).

The pharmaceutical composition can be present in a formulation in a unidose or multidose container and may be stored in a freeze dry condition which requires only the addition of a sterile liquid carrier.

Such pharmaceutical carrier could be in solid liquid or gaseous form and the suitable dose of administration and the ratio between the pharmaceutical carrier/active compound, varies according to the number of administration dose(s), the mass of the mammal to be treated and the possible side effects of the compound according to the invention upon said mammal.

The pharmaceutical composition according to the invention could be a therapeutic or prophylactic composition such as a vaccine.

The pharmaceutical composition according to the invention could be a suitable composition for allowing a vaccination against tick or various micro-organisms (viruses, bacteria or protozoa), transmitted by tick.

The present invention is also related to an immunological/vaccine formulation which comprises the polynucleotide according to the invention presented according to the techniques well-known by the person skilled in the art such as the one described by Wolff et al. (Science, Vol. 247, pp. 1465-1468 (1999)).

The pharmaceutical composition according to the invention could be used for treating or preventing any disease or pathogenesis involving leukotriene B4, such as Ischemy, atherosclerosis and in its ischemic complications (such as acute coronary syndromes and stroke), inflammatory diseases (such as chronic obstructive pulmonary disease, rheumatoid arthritis, septic shock), allograft rejection, cystic fibrosis, psoriasis, liver diseases, renal diseases, immunological and allergic disorders.

The vaccination against tick could be obtained by inducing a high rejection of tick and/or a neutralisation of the protection conferred by tick saliva to vectors transmitted by tick (viruses, bacteria or protozoa).

Another aspect of the present invention is related to a method of treatment or prevention of a disease affecting or supposed to affect a mammal (especially, live stock animals and humans) transmitted by tick, especially *Ixodes ricinus*, said method comprising the step of administrating to said mammal a sufficient amount of the pharmaceutical composition according to the invention in order to prevent or cure either the transmission of pathogenic agents by tick, especially *Ixodes ricinus*, or the symptoms of the disease(s) induced by said pathogenous agents (tick, viruses, bacteria or protozoa transmitted by the tick).

The present invention is also related to a method of treatment or prevention of arterial/venous related diseases or inflammation comprising the step of administrating to a mammal affected or supposed to be affected by said disease, a sufficient amount of the pharmaceutical composition according to the invention in order to prevent, reduce or cure the symptoms of said disease.

A final aspect of the present invention is related to the use of the pharmaceutical composition according to the invention for the manufacture of a medicament in the treatment and/or the prevention of various diseases, especially diseases induced by tick or pathogenous agents transmitted by tick, especially *Ixodes ricinus*, as well as for the treatment or the prevention of arterial/venous related diseases or inflammations.

The present invention is also related to a method for controlling the population of tick especially but not only *Ixodes ricinus* infesting animals (mammals, birds, reptiles and amphibians) by administrating to said animals a sufficient amount of the pharmaceutical composition according to the invention in order to avoid a blood meal by said tick.

Definitions

<<Polypeptide>> refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, PROTEINS—STRUCTURE AND MOLECULAR PROPERTIES, $2^{nd}$ Ed., T. E. Creighton, W. H. Freeman and Comany, New York, 1993 and Wolt, F., Posttranslational Protein Modifications Perspectives and Prospects, pp. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth. Enzymol.* (1990) 182:626-646 and Rattan et al., "Protein Synthesis: Posttranslational Modifications and Aging", *Ann NY Acad Sci* (1992) 663:48-62.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term "Polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA;

thus, "Polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more substitutions (preferably conservative), additions and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants should retain one or more of the biological activities of the reference polypeptide. For instance, they should have similar antigenic or immunogenic activities as the reference polypeptide. Antigenicity can be tested using standard immunoblot experiments, preferably using polyclonal sera against the reference polypeptide. The immunogenicity can be tested by measuring antibody responses (using polyclonal sera generated against the variant polypeptide) against purified reference polypeptide in a standard ELISA test. Preferably, a variant would retain all of the above biological activities.

"Sequence Identity" is a measure of the identity of nucleotide sequences or amino acid sequences. In general, the sequences are aligned so that the highest order match is obtained. "Sequence Identify" per se has an art-recognised meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds, Humana Press, New Jersey, 1994; SEQUENCE ANALYSIS IN MOLECULAR BIOLOGY, von Heijne, G., Academic Press, 1987; and SEQUENCE ANALYSIS PRIMER, Gribskov, M. and Devereux, J., eds, M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1998) 48:1073). Methods commonly employed to determine identity or similarity between two sequences include, but are not limited to those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCG program package (Devereux, J., et al., *J Molec Biol* (1990) 215:403). Most preferably, the program used to determine identity levels was the GAP program, as was used in the Examples hereafter.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Fragments of *I. ricinus* salivary gland polypeptides are also included in the present invention. A fragment is a polypeptide having an amino acid sequence that is the same as a part, but not all, of the amino acid sequence of the aforementioned *I. ricinus* salivary gland polypeptides. As with *I. ricinus* salivary gland polypeptides, fragment may be "free-standing" or comprised within a larger polypeptide of which they form a part or region, most preferably as a single continuous region. Representative examples of polypeptide fragments of the invention, include, for example, fragments from about amino acid number 1-20, 21-40, 41-60, 61-80, 81-100, and 101 to the end of the polypeptide. In this context "about" includes the particularly recited ranges larger or smaller by several, 5, 4, 3, 2 or 1 amino acid at either extreme or at both extremes.

Preferred fragments include, for example, truncated polypeptides having the amino acid sequence of the *I. ricinus* salivary gland polypeptides, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are fragments characterised by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate *I. ricinus* salivary gland protein activity, including those with a similar activity or an improved activity, or with a decreased undesirable activity. Also included are those that are antigenic or immunogenic in an animal or in a human.

The term "adjuvant" has its usual meaning in the art of vaccine technology, i.e. a substance or a composition of matter which is not in itself capable of mounting a specific immune response against the antigen of the vaccine, but which is nevertheless capable of enhancing the immune response against the antigen. In other words, the combination of vaccination with antigen and adjuvant induces an immune response against the antigen which is stronger than that induced by the antigen alone.

Suitable carriers for administration of vaccines are well known in the art and can include buffers, gels, microparticles, implantable solids, solvents, other adjuvants or any other means by which the antigen of the vaccine can be introduced into a subject and be made sufficiently available to produce an immune response to the antigen.

Examples of others adjuvant molecules are saponine or suitable fractions thereof and lipopolysaccharides as described in the document EP 671 948, saponine fractions with one or more sterols present in specific formulation are described in the document WO 2007/068907 in addition.

Other examples of adjuvants are metallic salts, oil in water emulsion, lipid and/or derivative thereof, aminoalkyl glucosaminide phosphate, immunostimulotary oligonucleotides QS21 or combination thereof possibly in association with liposome described in the document WO 2006/123155 or U.S. Pat. No. 6,544,518.

An adjuvant composition may also comprise proteins from the yersinia genus as described in document WO 02/304 58.

An adjuvant could comprise also one or more carrier molecule(s), such as metallic salt particles (aluminium phosphate, aluminium hydroxide, calcium phosphate, magnesium phosphate, iron phosphate, calcium carbonate, magnesium carbonate, calcium sulphate, magnesium hydroxide or double salt like ammonium-iron phosphate, potassium, iron phosphate, calcium iron phosphate, calcium magnesium carbonate or a mixture of these salts or polyporous polymeric particles (such as microbeads or nanoparticles (as described in document WO 02/30458)).

An adjuvant could correspond also to an immuno stimulatory CpG oligo nucleotide, preferably CpG oligo nucleotide having a length between 15 and 45 nucleotides.

The pharmaceutical composition (vaccine) may also comprise other compounds which are used for enhancing the antigenicity or immunogenicity of active compounds by addition of immuno modulators on immuno adjuvants such as a cytokines, interferons, tumor necrosis factors, transforming growth factors, or colony stimulating factors preferably interleukin-2. The immunogenicity of the pharmaceutical composition (vaccine) could be also induced by an adequate immuno adjuvant which is preferably selected from the group consisting of block copolymer, ethylene copolymer, acrylic acid copolymer, an acrylic acid copolymer emulsion, a mineral oil emulsion or a mixture thereof, (such as squalen or squalane).

The pharmaceutical composition (vaccine) of the invention is of any suitable pharmaceutical form. Suitable solid or liquid pharmaceutical forms are, for example, granules, powders, pill, tablets, capsules, suppositories, syrups, emulsions, suspensions, creams, aerosols, drops or injectable solution in ampoule form, in whose preparation excipients and additives such as disintegrants, binders, coating agents, swelling agents, lubricants, flavorings, sweeteners or solubilizers are customarily used. In the particular case of a slow-release composition, the pharmaceutical composition may comprise a biocompatible matrix suitable for slow-release.

Regarding the pharmaceutical carrier, in general, the nature of the carrier will depend on the particular mode of administration being employed. For instance, parenteral formulations usually comprise injectable fluids that include pharmaceutically and physiologically acceptable fluids such as water, physiological saline, balanced salt solutions, or the like as a vehicle. For solid compositions, conventional non-toxic solid carriers can include, for example, pharmaceutical grades of mannitol, lactose, or magnesium stearate. In addition to biologically-neutral carriers, pharmaceutical compositions to be administered can contain minor amounts of non-toxic additives, such as wetting or emulsifying agents, preservatives, and pH buffering agents and the like.

The route of administration of the vaccine or pharmaceutical composition according to the present invention can be any suitable route of administration. It can be topical, intradermal, subcutaneous, oral, intravenous, parenteral, intraperitoneal.

It is meant by a soluble leukotriene B4 receptor: a soluble compound which is able to bind specifically leukotriene B4 and to prevent the interaction of leukotriene B4 with its natural membrane receptors located at the surface of cells such as neutrophils.

EXAMPLES

1. Identification of the LTB4-LIR Polypeptide According to the Invention mRNAs were extracted from salivary glands of female ticks. After the blood meal, the mRNAs were purified with oligo-dT cellulose (Fasttrack 2.0 kit Invitrogen, Inc.). A reverse transcription has been made with an oligodT primer.

PCR reactions were made with the following forward primers: 5'-GCCACCATGCTTAGAATAGCGGTGGT-TGC-S' (SEQ ID NO: 3) and 5'-CTCGGGTCCCT-TGCGTTTGCA-S' (SEQ ID NO: 4).

PCR products were cloned into the vector pBlueBac4.5-V5-His TAG or pcDNA3.5-His TAG (Invitrogen), and the inserts were sequenced. This approach allows the recovering of a consensus sequence encoding a bioactive protein. The protein is hereafter identified as LTB4-LIR for "Leukotriene B4 binding Lipocalin from *Ixodes ricinus*".

Figure 1:
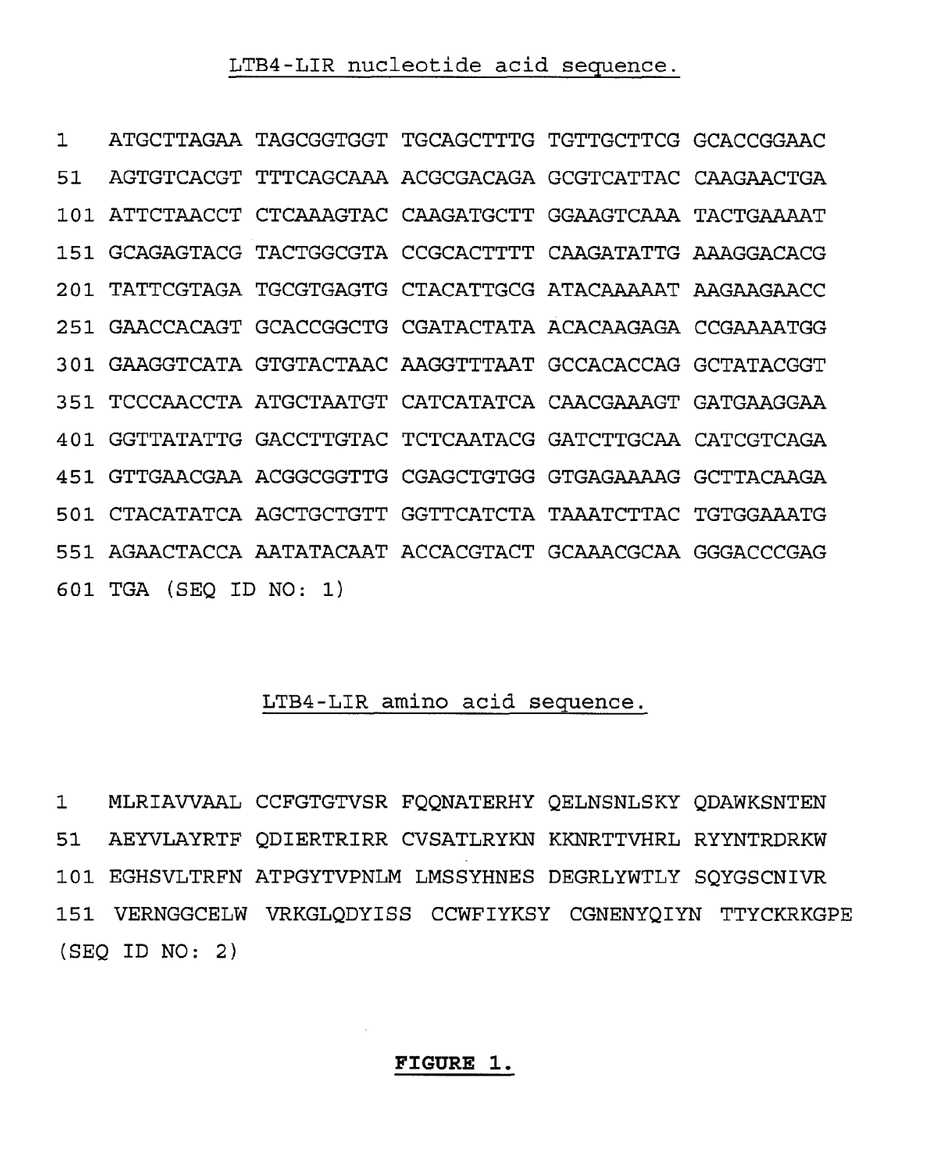
FIG. 1 represents the nucleotide (SEQ ID NO: 1) and amino acid (SEQ ID NO: 2) sequences of the LTB4-LIR.
Figure 2:
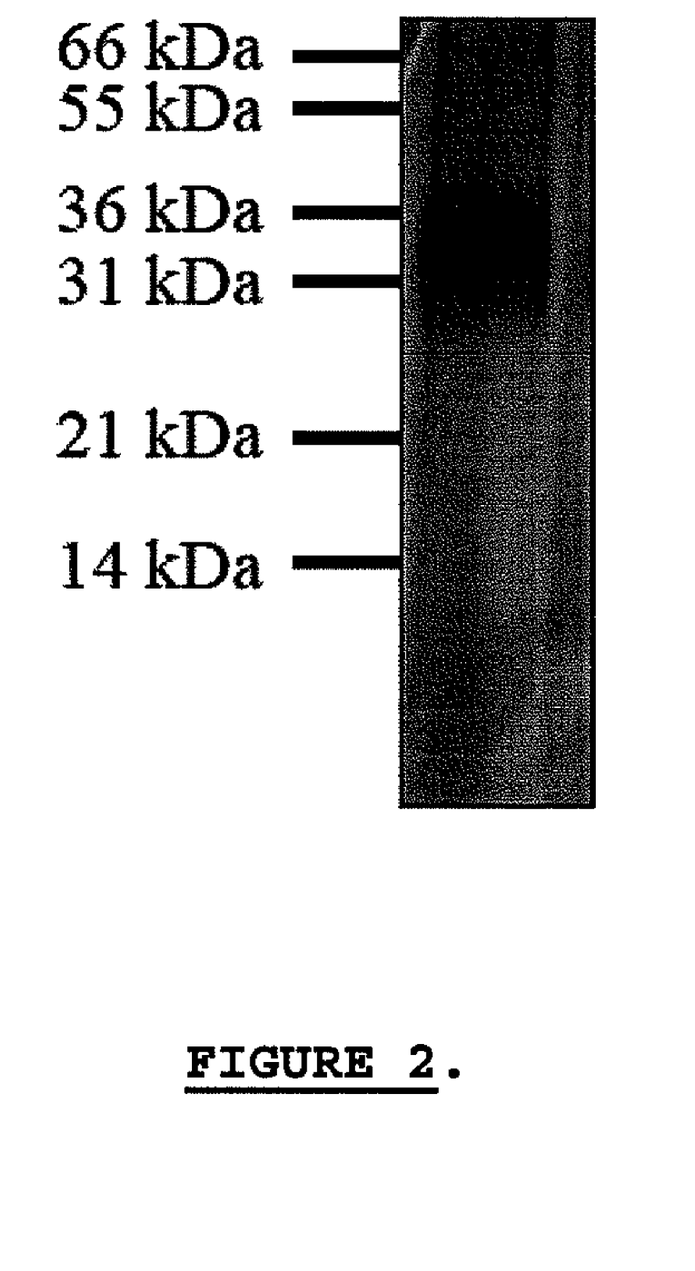
FIG. 2 represents affinity-purified LTB4-LIR migrated on a 10% SDS polyacrylamide gel.

Cloning and expression of the isolated cDNA for LTB4-LIR were achieved by transfection into insect cells. The coding sequence of LTB4-LIR polypeptide was inserted in the vector pBlueBac4.5-V5-His TAG in frame with the epitope V5-6×His tag, expressed in a baculovirus system and purified to homogeneity by affinity chromatography upon Ni-chelate columns as confirmed by SDS-PAGE (FIG. 2). Affinity-purified LTB4-LIR polypeptide migrated at an apparent weight of about 35 kDa on a 10% SDS polyacrylamide gel (FIG. 2), indicating that LTB4-LIR is highly glycosylated.

3. Binding Profiles of Various Eicosanoids to LTB4-LIR Polypeptide

The LTB4-LIR polypeptide was assigned to the lipocalin family by bioinformatic methods. This belonging was confirmed by the analysis of characteristics conserved in the lipocalin family. A 3D model was constructed by homology modeling using the structure of Rahbp2 (*Rhipicephalus appendiculatus* histamine binding protein) as template. This step required that LTB4-LIR and Rahbp2 are correctly aligned. The two proteins share only a few number of identical residues and the alignment consequently presented difficulties. However, information obtained by the analysis of the structurally conserved characteristics of the lipocalin family permitted to achieve a correct alignment. The fold comprises a 8-stranded β-barrel and two helices. The analysis of the 3D model suggested that the barrel of LTB4-LIR polypeptide could accommodate a fatty acid-like ligand in its cavity. Among the molecules involved in hemostasis and the immune response, the eicosanoids were the most probable ligands. This prediction has restrained the number of potential ligands and led to the experimental determination that LTB4-LIR polypeptide binds effectively leukotriene B4.

The polypeptide according to the invention was therefore tested for its ability to bind specifically leukotriene B4. The affinity-purified LTB4-LIR polypeptide was tested in binding assays according to a previously described method (Warlow, R. S., and Bernard, C. C. A. (1987). Solubilization and characterization of moderate and high affinity histamine binding sites on human blood mononuclear cells. Mol. Immunol. 24, 27-37).

Figure 3:
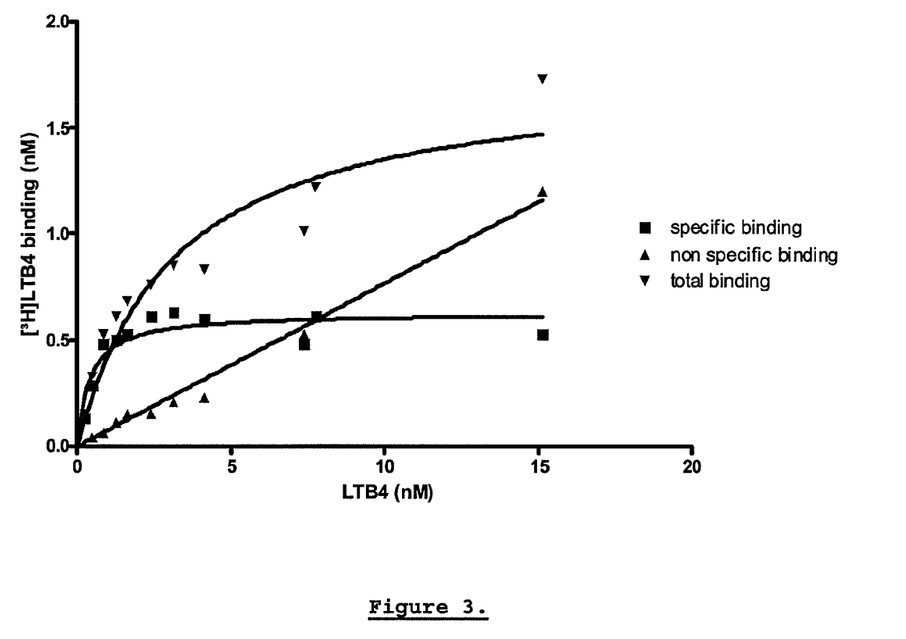
FIGS. 3 to 5 represent binding profiles of various eicosanoids to LTB4-LIR polypeptide.
Figure 4:
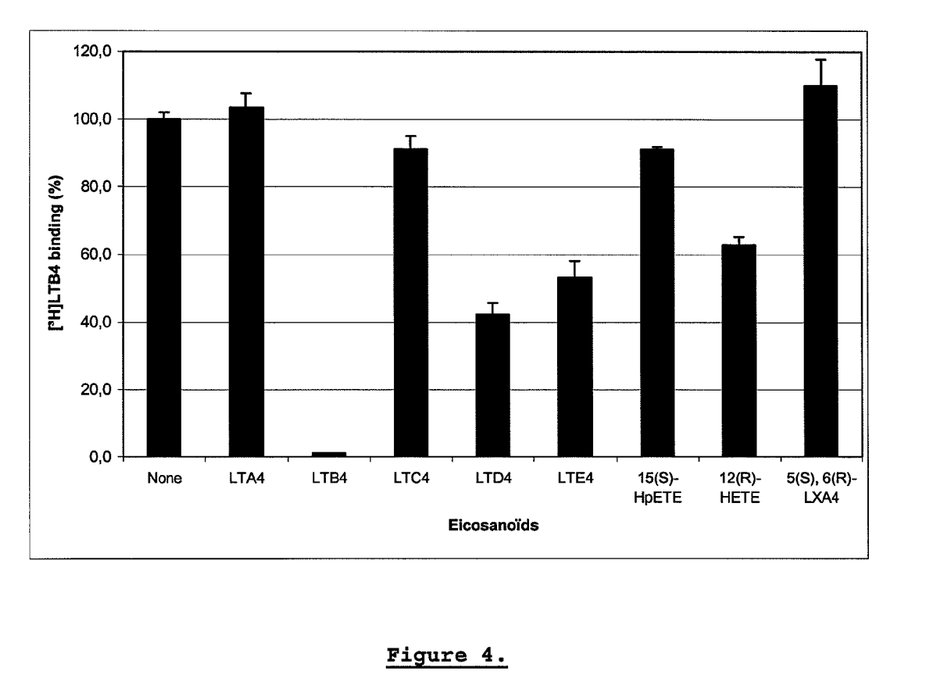
Figure 5:
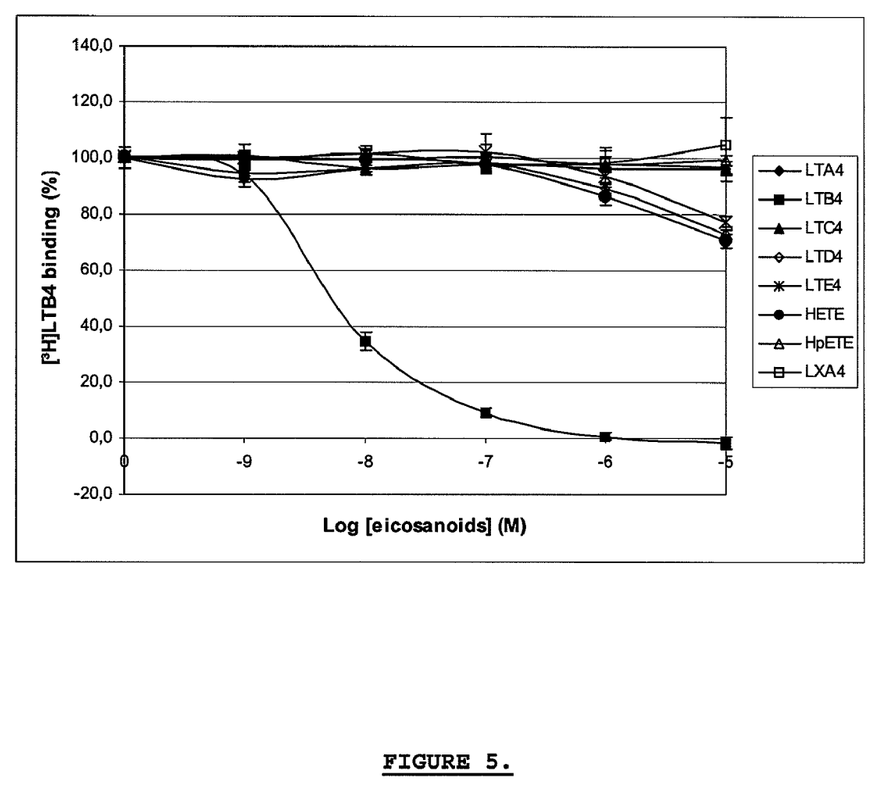

The LTB4-LIR polypeptide exhibits a specific and saturable binding for [3H]LTB4 with a Kd value of 0.4 nM (FIG. 3), which is lower than that for both known human BLT1 (by about 5 fold) and BLT2 (by about 60-fold) membrane receptors (Takehiko Yokomizo, Kazuhiko Katoi, Hiroshi Hagiya, Takashi Izumi, and Takao Shimizu. (2001). Hydroxye-icosanoids Bind to and activate the low affinity leukotriene B4 receptor, BLT2. J. Biol. Chem. 276, 12454-12459). The inhibition by various eicosanoids of [3H]LTB4 binding to LTB4-LIR polypeptide was also examined. FIG. 4 shows the inhibition of 1 nM [3H]LTB4 binding by various eicosanoids at a concentration of 10 μM. LTB4 binding to LTB4-LIR polypeptide is very specific, because only LTB4, LTD4, LTE4 and 12(R)-HETE showed significant competitions at this concentration. Next, various concentrations of LTA4, LTB4, LTC4, LTD4, HETE, HPETE, and LXA4 was tested in the competition with [3H]LTB4 binding to LTB4-LIR polypeptide. Only LTB4 shows dose-dependent inhibition of LTB4 [3H]LTB4 binding to LTB4-LIR polypeptide (FIG. 5).

4. Effect of LTB4-LIR Polypeptide on the Chemo-attraction of Neutrophils

The principal LTB4 function is the chemo-attraction of neutrophils to the sub-endothelial spaces of an inflammation site. One step of this process is the diapedesis of the neutrophils through the endothelial cells layer. The chemo-attractant effect of LTB4-LIR6 was tested by using a model of transendothelial migration of neutrophils.

Ea.hy926 cells, an endothelial cell line derived from the human umbilical vein, were used. These cells closely resemble HUVEC and maintain several characteristics of differentiated endothelium. The cells were allowed to reach confluence in chamber containing DMEM (Cambrex, Vervier, Belgium), supplemented with 10% Fetal Calf Serum, 2 mM L-Glutamine, 100 U/ml penicillin, 100 μg/ml streptomycin and HAT (1000 μM hypoxanthine, 0.4 μM aminopterin, 16 μM thymidine). Neutrophils isolation (Takahashi A., Yamamoto K., Okuma M., Sasada M. Transient calcium elevation in polymorphonuclear leukocytes triggered by thrombin-activated platelets. Eur. J. Haematol., 1992 (48): 196-201)

Neutrophils were prepared from peripheral blood from healthy volunteers. Citrated blood was mixed with an equal volume of 6% dextran/0.9% NaCl solution and allowed to stand for 1 hour at room temperature. Then neutrophils fraction was recovered and spin at 220 g for 12 minutes at 4° C. Afterwards, pellet was resuspended in ammonium chloride and after 15 minutes, spin at 280 g for 6 minutes at 4° C. This step was repeated until no red blood cells remain. Purity of preparation was >90% neutrohils as judged by Cell-dyn 1600 (Abbott) and by morphological examination with May-Grün-wald Giemsa staining.

Figure 6:
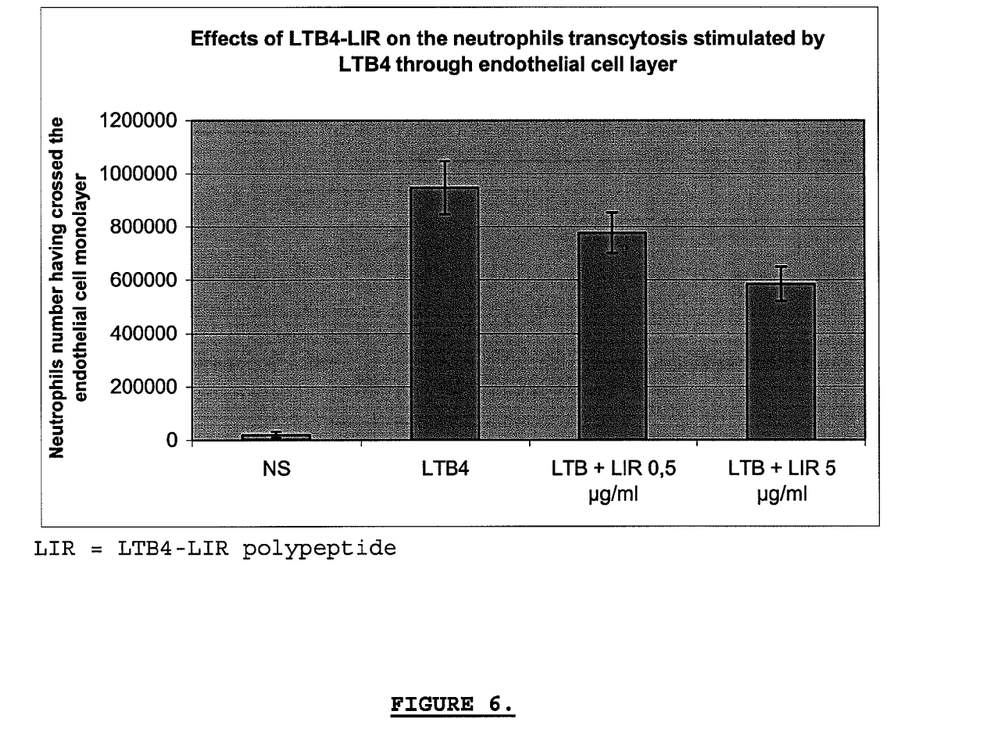
FIG. 6 represents the effect of LTB4-LIR polypeptide on the neutrophils transcytosis stimulated by LTB4 through endothelial cell layer.

In the transendothelial assay, the protocol described by Nohgawa et al. was used (Nohgawa M., Sasada M., Maeda A., Asagoe K., Harakawa N., Takano K., Yamamoto K., Okuma M. Leukotriene B4-activated human endothelial cells promote transendothelial neutrophil migration. J Leuc. Biol, 1997 (62): 203-209). In brief, neutrophils were resuspended at a concentration of $5 \times 10^6$ cells/ml in RPMI containing 10% FBS and were added to the upper chamber above the endothelial cell monolayer. The same medium with or without LTB4 and/or LTB4-LIR was put in the assay. After 2 hours at 37° C., the upper chambers were removed and cells in lower chambers were counted. Results were obtained using blood neutrophils from three volunteers, in triplicate (FIG. 6). These results indicated that a significant dose-response effect of LTB4-LIR on the transendothelial migration of neutrophils stimulated by LTB4.

The invention claimed is:

1. A pharmaceutical composition comprising a pharmaceutical carrier and a polypeptide which presents more than 95% sequence identity with the amino-acid sequence SEQ ID NO: 2, wherein the polypeptide comprises leukotriene B4 binding activity.

2. The composition according to the claim 1, wherein the polypeptide presents more than 98-99% sequence identity with the amino-acid sequence SEQ ID NO: 2.

3. The composition according to the claim 1, wherein the polypeptide is a leukotriene B4 binding polypeptide consisting of the amino-acid sequence of SEQ ID NO: 2 or an active leukotriene B4 binding fragment thereof.

4. A method of treating inflammation in a mammal, comprising administering to the mammal a therapeutically effective amount of the pharmaceutical composition according to claim 1, wherein the inflammation is associated with leukotriene B4 activation of inflammatory cells.

5. An isolated polypeptide which presents more than 95% sequence identity with the amino-acid sequence SEQ ID NO: 2, wherein the polypeptide comprises leukotriene B4 binding activity.

6. The isolated polypeptide according to the claim 5 which presents more than 98-99% sequence identity with the amino-acid sequence SEQ ID NO: 2.

7. An isolated leukotriene B4 binding polypeptide consisting of the amino-acid sequence of SEQ ID NO: 2 or an active leukotriene B4 binding fragment thereof.

8. An in vitro method of inhibiting transendothelial migration of neutrophils stimulated by leukotriene B4 through a mammalian transendothelial cell layer, the method comprising contacting the cell layer with a polypeptide comprising the amino acid sequence of SEQ ID NO: 2, thereby inhibiting transendothelial migration of neutrophils stimulated by leukotriene B4.

* * * * *